United States Patent

Santaniello et al.

[11] Patent Number: 5,525,627
[45] Date of Patent: Jun. 11, 1996

[54] ESTERS OF ACYL CARNITINES WITH LONG-CHAIN ALIPHATIC ALCOHOLS AND PHARMACEUTICAL COMPOSITIONS CONTAINING SAME HAVING ANTIMYCOTIC ACTIVITY

[75] Inventors: Mosè Santaniello, Casoria; Maria O. Tinti; Domenico Misiti, both of Rome; Piero Foresta, Pomezia, all of Italy

[73] Assignee: Sigma-Tau Industrie Farmaceutiche Riunite S.p.A., Rome, Italy

[21] Appl. No.: 409,714

[22] Filed: Mar. 24, 1995

Related U.S. Application Data

[62] Division of Ser. No. 250,108, May 26, 1994, Pat. No. 5,519,056, which is a continuation of Ser. No. 714, Jan. 5, 1993, abandoned.

Foreign Application Priority Data

Jan. 16, 1992 [IT] Italy ................. RM92A0028

[51] Int. Cl.⁶ .................................. A61K 31/275
[52] U.S. Cl. .............................. 514/547; 560/170
[58] Field of Search ..................... 514/547; 560/170

[56] References Cited

U.S. PATENT DOCUMENTS

| | | | |
|---|---|---|---|
| 4,018,821 | 4/1977 | Tenud | 560/170 |
| 4,021,480 | 5/1977 | Tenud | 560/170 |
| 4,439,438 | 3/1984 | Cavazza | 560/170 |
| 4,443,475 | 4/1984 | Cavazza | 560/170 |
| 4,551,477 | 11/1985 | Cavazza | 560/170 |

FOREIGN PATENT DOCUMENTS

| | | | |
|---|---|---|---|
| 2096136 | 10/1982 | United Kingdom | 560/170 |

*Primary Examiner*—Michael L. Shippen
*Attorney, Agent, or Firm*—Oblon, Spivak, McClelland, Maier & Neustadt

[57] ABSTRACT

Esters of acyl L-carnitines of general formula (I)

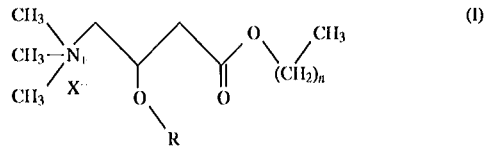

wherein R is a straight or branched acyl group having 2 to 16 carbon atoms, in particular isobutyryl and isovaleryl;

n is an integer comprised between 7 and 15, particularly 10; and,

X- is the anion of a pharmacologically acceptable acid are endowed with potent antimycotic activity particularly against yeast like fungi, such as *Candida albicans*, the aetiologic agent of candidiasis and against filamentous fungi, such as *Aspergillus fumigatus*, the aetiologic agent of aspergillosis. Orally or parenterally administrable or topically applicable pharmaceutical compositions comprise an ester of formula (I) as active ingredient.

10 Claims, No Drawings

ESTERS OF ACYL CARNITINES WITH LONG-CHAIN ALIPHATIC ALCOHOLS AND PHARMACEUTICAL COMPOSITIONS CONTAINING SAME HAVING ANTIMYCOTIC ACTIVITY

This is a division, of application Ser. No. 08/250,108, filed on May 26, 1994, now U.S. Pat. No. 5,519,056, which is a continuation of application Ser. No. 08/000,714, filed on Jan. 5, 1993, now abandoned.

The present invention relates to esters of acyl L-carnitines with long-chain aliphatic alcohols, of general formula (I)

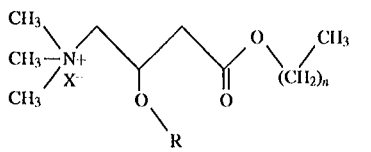

wherein R is a straight or branched saturated carboxylic acyl group having from 2 to 16, preferably from 4 to 12, carbon atoms, in particular isobutyryl and isovaleryl;

n is an integer from 7 to 15, particularly 10, and

X- is the anion of a pharmacologically acceptable acid.

Among the esters of formula (I) isovaleryl L-carnitine undecil ester and isobutyryl L-carnitine undecil ester are particularly preferred.

Therefore, the present invention also relates to orally or parenterally administrable or topically applicable pharmaceutical compositions useful for the treatment of infections such as candidiasis, cryptococcosis and aspergillosis sustained by pathogenic fungi.

Crytpococcosis is an infection of the respiratory tract, generally asymptomatic and benign which may provoke a systemic spread and serious cephalomeningitis in both wasted and even healthy subjects. The disease is due to the fungus *Cryptococcus neoformans* (now known as *Filobasidiella neoformans*) widely distributed in nature, which can be transmitted to humans via inhalation.

Candidiasis encompasses a wide range of mycoses varying from common infections of the skin and mucous membranes to life-threatening systemic infections. These infections are due to some strains belonging to the genus Candida, particularly *C. albicans*.

*C. albicans* is one of the most widely occurring constituents of the microbial flora of various mucosas such as that of vagina, mouth and digestive tract, where under conditions particularly unfavourable to the host but optimal for the fungus growth (such as debilitating affections, prolonged administration of antibiotics and corticosteroids, etc.) it may bring about life-threatening pathologies.

The main affections induced by this fungus are: vulvovaginitis, dissemination to the lungs (pneumonia) and other organs such as kidney, spleen, eyes, meninges, liver, intestine and endocardium, as complication of preexisting diseases; thrush frequently occurring in newborns and young adults (characterized by creamy white patches on the buccal mucosa); cutaneous candidiasis and onychomycosis.

Aspergillosis, an infectious disease caused by the inhalation of spores of the genus Aspergillus (fumigatus, flavus), is a serious and invasive pulmonary infection brought about by the growth of a fungal colony which frequently fills preexisting cavities, such as pulmonary abscesses.

Aspergillus spp (e.g. *A. niger*) may also cause otomycosis. Serious intoxications (mycotoxicosis) in animals, fed on contaminated fodder, are caused by the toxins (aflatoxins) produced by *Aspegillus flavus*. *Aspergillus flavus* is suspected to cause cirrhosis and liver cancer in humans, in areas wherein foodstuffs are likely to be contaminated by aflatoxins.

The esters of formula (I) may be prepared following two distinct synthesis processes. The first process (illustrated in the synthesis scheme 1) comprises the steps consisting of:

(a) halogenating an acyl L-carnitine with a halogenating agent, such as thionyl chloride and oxalyl chloride (molar ratio comprised between 1:1 and 1:4) in an anhydrous organic inert solvent such as acetonitrile or methylene chloride at a temperature comprised between 0° C. and 30° C. for 1–4 hours, concentrating the raw reaction product and using it in the following step;

(b) dissolving the acid chloride of step (a) in an anhydrous organic inert solvent such as acetonitrile or methylene chloride and adding the alcohol diluted in the same solvent at a ratio comprised between 1:1 and 1:2, at a temperatures comprised between 0° C. and 30° C. for 2–10 hours, concentrating the solution and, if needed, purifying the compound by chromatography on silica gel; and (c) eluting the product dissolved in water or in an organic solvent on a strongly basic ion exchange resin such as Amberlite IRA 402 or on a weakly basic ion exchange resin such as Amberlist A 21, activated with the desired HX acid and isolating the end product by lyophilization or concentration.

The second process (illustrated in the synthesis scheme 2) comprise the steps consisting of:

(a') reacting carnitine or an acyl carnitine inner salt with the relevant alkyl halogenide (preferably bromide or iodide) in an organic anhydrous inert solvent at a temperature comprised between 30° C. and 60° C. for 8–24 hours and then isolating the resulting compound by concentration;

(b') acylating the ester obtained in step (a') with the desired acid chloride by known techniques, in case the starting compound in step (a') is carnitine;

(c') eluting an aqueous or alcoholic solution of the compound of step (a') or (b') on an ion exchange resin, such as Amberlite IRA 402 or Amberlist A 21 activated with the desired HX acid.

The anion X- of the pharmacologically acceptable acid is preferably selected from chloride; bromide; iodide; aspartate, particularly acid asparatate; citrate, particularly acid citrate; tartrate; phosphate, particularly acid phosphate; fumarate, particularly acid fumarate; glycerophosphate; glucosephosphate; lactate; maleate, particularly acid maleate; orotate; oxalate, particularly acid oxalate; sulphate, particularly acid sulphate; trichloroacetate; trifluoroacetate and methansulphonate.

SYSTHESIS SCHEME 1

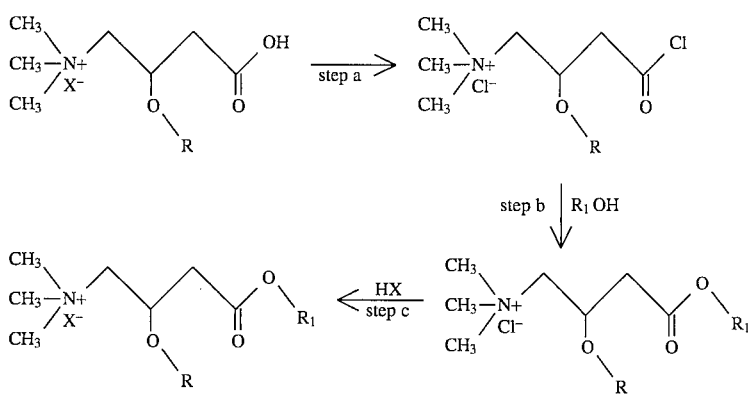

R = acyl

R₁ = alkyl having 11–16 carbon atoms

SYSTHESIS SCHEME 2

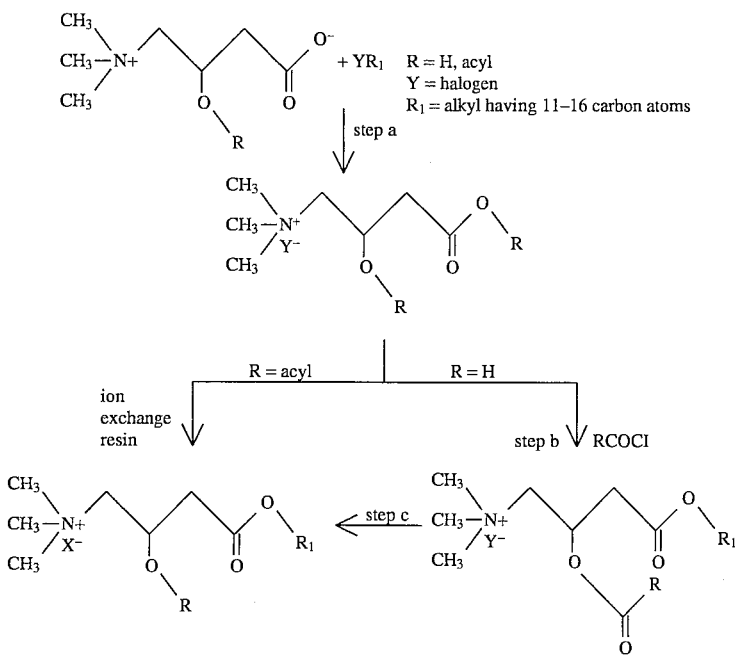

EXAMPLE 1

PREPARATION OF ISOVALERYL-L-CARNITINE UNDECYL ESTER CHLORIDE (ST 722)

Step A Preparation of isovaleryl-L-carnitine chloride acid chloride.

Isovaleryl-L-carnitine chloride (30 g; 0.106 moles) was suspended in 100 ml anhydrous $CH_2Cl_2$.

The mixture was cooled at 0° C. and oxalyl chloride (13 ml; 0.15 moles) diluted in 15 ml anhydrous $CH_2Cl_2$ was slowly added under stirring.

After 30 minutes at room temperature, a further amount of oxalyl chloride (19 ml; 0.21 moles) diluted in 10 ml anhydrous $CH_2Cl_2$ was added.

The resulting solution was kept under stirring for 2 hours at room temperature, then concentrated under vacuum.

The residue thus obtained was washed twice with anhydrous $CH_2Cl_2$ and concentrated under vacuum.

The raw product thus obtained was used as such in the next reaction.

Step B: Preparation of isovaleryl-L-carnitine undecyl ester chloride (ST 722).

The acid chloride previously prepared (0.106 moles) was dissolved in anhydrous $CH_2Cl_2$ (40 ml).

The solution was cooled at 0° C. and undecylic acid (35 ml; 0.168 moles) diluted in 35 ml $CH_2Cl_2$ was added in a nitrogen atmosphere.

The solution was kept under stirring at room temperature for 2 hours and then concentrated under vacuum until an oily residue was obtained.

The raw reaction mixture was chromatographed on a silica gel column buffered with 2% $Na_2HPO_4$, eluting with $CH_2Cl_2$ till complete elution of undecylic alcohol and then with $CH_2Cl_2$-MeOH 9:1 till complete elution of the compound.

The pooled fractions were concentrated and gave 28 g of the title compound; Yield 60%.

$[\alpha]_D^{25} = -10.5$ (c=1% $H_2O$))

| Elementary analysis for $C_{23}H_{46}ClNO_4$ | | | | |
|---|---|---|---|---|
| | C % | H % | Cl % | N % |
| Calculated (anhydrous) | 63.35 | 10.63 | 8.13 | 3.21 |
| Found | 60.87 | 0.88 | 8.14 | 3.29 |

$H_2O$ 2.4%
HPLC
Column: Spherisorb Cl 5 μm
t.: 50° C.
Eluant: $CH_3OH/KH_2PO_4$ 50 mM (65:35)
Flow rate: 1 ml/min.
Retention time: 14.82 min
NMR CDCl3 δ5.5 (1H,m,—CH—); 4.2-3.8(4H,m,N+$CH_2$; $OCH_2$); 3.3(9H,S,$(CH_3)_3$N+); 2.8(2H,m,$CH_2$COO); 2.2(2H, m,$OCOCH_2$); 1.6-1.0(22H,m

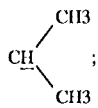

$(CH_2)_9CH_3$); 0.8(6H,d)

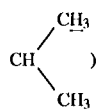

EXAMPLE 2

PREPARATION OF ISOBUTYRYL-L-CARNITINE UNDECYL ESTER CHLORIDE (ST 712)

The compound was prepared as described in example 1, substituting isobutyryl L-carnitine chloride for isovaleryl L-carnitine chloride. Yield 55%.

$[\alpha]_D^{25} = -15.8$ (c=1% $H_2O$)

| Elementary analysis for $C_{22}H_{44}O_4NCl$ | | | | |
|---|---|---|---|---|
| | C % | H % | Cl % | N % |
| Calculated (anhydrous) | 62.61 | 10.51 | 3.32 | 8.40 |
| Found | 61.77 | 10.67 | 3.29 | 8.17 |

$H_2O$ 0.8%
HPLC
Column: Spherisorb Cl (4.6 mm)
eluant $CH3OH$-$KH_2$ $PO_4$ 50 mM 60-40
Flow rate: 1 ml/min
Retention time: 14,75 min
NMR $CDCl_3$ δ5.5 (1H,m);

4.2-3.8(4H,m,N+$CH_2$-;$OCH_2$); 3.3 (9H,s,$(CH_3)_3$N+); 2.8(2H,m,$CH_2$COO); 2.5 (1H,m,COCH); 1.5-0.9 (27H,m

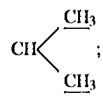

$(CH_2)_9$-$CH_3$

EXAMPLES 3–19

The compounds of Examples 3–19 were prepared following the procedures of the previous examples, as apparent to any average expert in organic synthesis. The physico-chemical characteristics of the compounds are summarized in the following table.

| Ex code | R | n | X | $[\alpha]_D^{25}$ | E.A. found | | | | | m.p. °C. | HPLC Rt min | NMR δ |
|---|---|---|---|---|---|---|---|---|---|---|---|---|
| | | | | | C | H | N | Cl | $H_2O$ | | | |
| 3 ST 1000 | octanoyl | 10 | Cl | -10,7 (c=1% $CHCl_3$) | $C_{26}H_{52}NO_4Cl$ 62,84% | 10,7% | 3,03% | 6,96% | 3,2% | 103-105 | 10,28ª | 5,7(1H, m, CHO); 4,3-4,0(4H, m, $CH_2N^+$; $OCH_2$); 3,5(9H, s, $(CH_3)_3N^+$); 2,8(2H, m, $CH_2$COO); 2,3(2H, t, $OCOCH_2$); 1,8(4H, m, 2$CH_2$); 1,6(4H, m; 2$CH_2$); 1,3(20H, broad, 10$CH_2$); 0,9(6H, 2t, 2$CH_3$).$CDCl_3$ |
| 4 ST 982 | undecanoyl | 10 | Cl | -14 (c=0,5% MeOH) | $C_{29}H_{58}NO_4Cl$ 66,65% | 11,72% | 2,70% | 6,93% | 0,4% | 133-135 | 16,32ᵇ | 5,6(1H, m, CHO); 4,1(2H, t, $OCH_2$); 3,9-3,7(2H, m, $CH_2N^+$); 3,3(9H, s, $(CH_3)_3N^+$); 2,8(2H, dd, $CH_2$COO); 2,4(2H, t, $OCOCH_2$); 1,6(4H, m, 2$CH_2$); |

-continued

| Ex code | R | n | X⁻ | $[\alpha]_D^{25}$ | E.A. found | | | | | m.p. °C. | HPLC Rt min | NMR δ |
|---|---|---|---|---|---|---|---|---|---|---|---|---|
| | | | | | C | H | N | Cl | H₂O | | | |
| 5 ST983 | palmitoyl | 10 | Cl⁻ | −14 (c = 1% MetOH) | 69,42% | 11,84% | $C_{34}H_{68}NO_4Cl$ 2,36% | 5,96% | 0,8% | 158–159 | 10,5$^e$ | 1,3(30H, broad, 15CH₂); 0,9(6H, t, 2CH₃).CD₃OD 5,6(1H, m, CHO); 4,1(2H, t, OCH₂); 3,9-3,7(2H, m, CH₂N⁺); 3,2(9H, s, (CH₃)₃N⁺); 2,8(2H, m, CH₂COO); 2,4(2H, t, OCOCH₂); 1,6(4H, m, 2CH₂); 1,3(40H, broad, 20CH₂); 0,9(6H, t, 2CH₃).CD₃OD |
| 6 ST 1034 | isocaproyl | 10 | Cl⁻ | −13,12 (c = 0,8% H₂O) | 61,28% | 11,10% | $C_{24}H_{48}NO_4Cl$ 3,12% | 9,01% | 1,9% | oil/not determined | 8,45$^d$ | 5,7(1H, m, CHO); 4,1(2H, t, OCH₂); 4,0-3,7(2H, m, CH₂N⁺); 3,2(9H, s, (CH₃)₃N⁺); 3,0-2,7(2H, m, CH₂COO); 2,6-2,3(2H, m, OCOCH₂); 1,7-1,4(5H, m, 2CH₂, —CH); 1,3(16H, broad, 8CH₂); 0,9(6H, d, (CH₃)₂); 0,8(3H, t, CH₃).D₂O |
| 7 ST 1036 | heptanoyl | 10 | Cl⁻ | −12,1 (c = 1% H₂O) | 64,35% | 12,55% | $C_{25}H_{49}NO_4Cl$ 3,09% | 6,68% | 1,3% | not determined | 9,35$^d$ | 5,7(1H, m, CHO); 4,1(2H, t, OCH₂); 4,0-3,7(2H, m, CH₂N⁺); 3,2(9H, s, (CH₃)₃N⁺); 3,0-2,7(2H, m, CH₂COO); 2,5-2,3(2H, m, COCH₂); 1,6(4H, m, 2CH₂); 1,3(22H, m, 11CH₂); 0,9-0,8(6H, 2t, 2CH₃).D₂O |
| 8 ST 1050 | heptanoyl | 12 | Cl⁻ | −10,3 (c = 0,7% CHCl₃) | 65,26% | 11,62% | $C_{27}H_{54}NO_4Cl$ 2,87% | 6,70% | 0,3% | dec. 150–160 | 9,13$^e$ | 5,7(1H, m, CHO); 4,3-4,0(4H, m, CH₂N⁺; OCH₂); 3,5(9H, s, (CH₃)₃N⁺); 2,8(2H, m, CH₂COO); 2,3(2H, m, OCOCH₂); 1,6(4H, m, 2CH₂); 1,3(26H, m, 13CH₂); 0,9(6H, 2t, 2CH₃).CDCl₃ |
| 9 ST 1051 | 2-methyl hexanoyl | 12 | Cl⁻ | −8,8 (c = 1% CHCl₃) | 65,06% | 11,32% | $C_{27}H_{54}NO_4Cl$ 2,91% | 6,93% | 0,4% | not determined | 28,03$^b$ | 5,7(1H, m, CHO); 4,3-4,0(4H, m, CH₂N⁺; OCH₂); 3,5(9H, s, (CH₃)₃N⁺); 2,8(2H, m, CH₂COO); 2,4(1H, m, CH); 1,6(2H, m, CH₂); 1,3(26H, m, 13CH₂); 1,1(3H, m, CHCH₃); 0,9(6H, 2t, 2CH₃).CDCl₃ |
| 10 ST 1033 | isovaleryl | 12 | Cl⁻ | −11,8 (c = 1% H₂O) | 63,73% | 12,50% | $C_{25}H_{50}NO_4Cl$ 3,17% | 7,03% | 1,2% | dec. 150 | 9,39$^d$ | 5,7(1H, m, CHO); 4,1(2H, m, OCH₂); 4,0-3,7(2H, m, CH₂N⁺); 3,2(9H, s, (CH₃)₃N⁺); 3,0-2,7(2H, m, CH₂COO); 2,3(2H, m, OCOCH₂); 2,1(1H, m, CH₂CH); 1,6(2H, m, CH₂); 1,3(20H, broad, 11CH₂); 0,9(6H, dd, CH(CH₃)₂); 0,8(3H, t, CH₃).D₂O |
| 11 ST 1052 | hexanoyl | 12 | Cl⁻ | −10,7 (c = 1% CHCl₃) | 65,01% | 11,87% | $C_{26}H_{52}NO_4Cl$ 2,93% | 7,14% | 1,2% | dec. 120–130 | 14,86$^e$ | 5,7(1H, m, CHO); 4,3-4,0(4H, m, CH₂N⁺; OCH₂); 3,5(9H, s, (CH₃)₃N⁺); 2,9-2,7(2H, m, CH₂COO); 2,3(2H, t, OCOCH₂); 1,6(4H, m, 2CH₂); 1,3(24H, broad, 12CH₂); 0,9(6H, m, 2CH₃).CDCl₃ |
| 12 ST 1053 | octanoyl | 12 | Cl⁻ | −9,8 (c = 1% CHCl₃) | 66,46% | 11,93% | $C_{28}H_{56}NO_4Cl$ 2,71% | 6,93% | 0,7% | dec. 150–160 | 14,71$^e$ | 5,7(1H, m, CHO); 4,3-4,0(4H, m, CH₂N⁺; OCH₂); 3,5(9H, s, (CH₃)₃N⁺); 2,9-2,7(2H, m, CH₂COO); 2,3(2H, m, OCOCH₂); |

-continued

| Ex code | R | n | X | $[\alpha]_D^{25}$ | E.A. found | | | | | m.p. °C. | HPLC Rt min | NMR δ |
|---|---|---|---|---|---|---|---|---|---|---|---|---|
| | | | | | C | H | N | Cl | H$_2$O | | | |
| 13 ST 1037 | isovaleryl | 11 | Cl⁻ | −12,2 (c = 1% H$_2$O) | C$_{24}$H$_{48}$NO$_4$Cl 63,46% 12,26% 3,15% 7,81% 1,0% | | | | | dec. 150-160 | 12,65$^a$ | 1,6(4H, m, 2CH$_2$); 1,3(28H, broad, 14CH$_2$); 0,9(6H, m, 2CH$_3$).CDCl$_3$ 5,7(1H, m, CHO); 4,4-4,0(4H, m, N⁺CH$_2$; OCH$_2$); 3,5(9H, s, N⁺(CH$_3$)$_3$); 2,8(2H, m, CH$_2$COO); 2,2(2H, m, OCOCH$_2$); 2,0(1H, m, CH(CH$_3$)$_2$); 1,6(2H, m, CH$_2$); 1,2(18H, broad, 9(CH$_2$); 0,9-0,8(9H, d,t, CH$_3$; (CH$_3$)$_2$).CDCl$_3$ |
| 14 ST 1038 | isobutyryl | 11 | Cl⁻ | −14,5 (c = 1% H$_2$O) | C$_{23}$H$_{46}$NO$_4$Cl 62,90% 11,47% 3,27% 7,86% 0,4% | | | | | dec. 150-155 | 14,0$^a$ | 5,7(1H, m, CHO); 4,4-4,0(4H, m, N⁺CH$_2$; OCH$_2$); 3,5(9H, s, N⁺(CH$_3$)$_3$); 2,9-2,7(2H, m, CH$_2$COO); 2,6-2,5(1H, m, CH(CH$_3$)$_2$); 1,6(2H, m, CH$_2$); 1,3(18H, broad, 9CH$_2$); 1,1(6H, d, CH(CH$_3$)$_2$); 0,8(3H, t, CH3).CDCl3 |
| 15 ST 1060 | heptanoyl | 11 | Cl⁻ | −12,7 (c = 1% MetOH) | C$_{26}$H$_{52}$NO$_4$Cl 67,00% 12,12% 2,41% 6,60% 0,6% | | | | | not determined | 10,47$^f$ | 5,7(1H, m, CHO); 4,4-4,0(4H, m, N⁺CH$_2$; OCH$_2$); 3,5(9H, s, N⁺(CH$_3$)$_3$); 2,8(2H, m, CH$_2$COO); 2,4(2H, t, COOCH$_2$) 1,6(2H, m, CH$_2$); 1,3(26H, broad, 13CH$_2$); 0,9(6H, 2t, 2CH$_3$) |
| 16 ST 1001 | isovaleryl | 15 | Cl⁻ | −12,6 (c = 0,5% H$_2$O) | C$_{28}$H$_{56}$NO$_4$Cl 65,30% 11,11% 2,68% 7,57% 0,5% | | | | | not determined | 12,12$^a$ | 5,7(1H, m, CHO); 4,4-4,0(4H, m, N⁺CH$_2$; OCH$_2$); 3,5(9H, s, N⁺(CH$_3$)$_3$); 2,8(2H, m, CH$_2$COO); 2,2(3H, m, CH(CH$_3$)$_2$); 1,6(2H, m, CH$_2$); 1,3(26H, broad, 13CH$_2$); 1,0-0,9(9H, d,t, CH$_3$,CH(CH$_3$)$_2$).CDCl$_3$ |
| 17 ST 1018 | isovaleryl | 10 | tartrate acid | −1,9 (c = 1% H$_2$O) | C$_{27}$H$_{51}$NO$_{10}$ 56,87% 9,78% 2,44% | | | | 4% | not determined | 13,74$^a$ | 5,7(1H, m, CHO); 4,5(2H, s, 2CHOH); 4,1-3,6(4H, m, N⁺CH$_2$; OCH$_2$); 3,2(9H, s, N⁺(CH$_3$)$_3$); 3,0-2,7(2H, m, CH$_2$COO); 2,4-2,2(2H, m, OCOCH$_2$); 2,1-2,0(1H, m, CH(CH$_3$)$_2$); 1,6(2H, m, CH$_2$); 1,3(16H, broad, 8CH$_2$); 0,9(6H, d, CH(CH$_3$)$_2$); 0,8(3H, t, CH$_3$).D$_2$O |
| 18 ST 1017 | isovaleryl | 10 | fumarate acid | −13,3% (c = 1% H$_2$O) | C$_{27}$H$_{49}$NO$_8$ 62,23% 9,90% 2,54% | | | | 0,7% | dec. 120 | 13,99$^a$ | 6,6(2H, s, CH=CH); 5,7(1H, m, CHO); 4,1-3,7(4H, m, N⁺CH$_2$; OCH$_2$); 3,2(9H, s, N⁺(CH$_3$)$_3$); 3,0-2,7(2H, m, CH$_2$COO); 2,4-2,2(2H, m, OCOCH$_2$); 2,0(1H, m, CH(CH$_3$)$_2$); 1,6(2H, m, CH$_2$); 1,3(16H, broad, 8CH$_2$); 0,9(6H, t, CH(CH$_3$)$_2$); 0,8(3H, t, CH$_3$).D$_2$O |
| 19 ST 1032 | isovaleryl | 8 | Cl⁻ | −17,4% (c = 1% H$_2$O) | C$_{20}$H$_{40}$ClNO$_4$ 59,93% 10,25% 3,49% 8,84% 1,7% | | | | | not determined | 5,75$^b$ | 5,7(1H, m, CHO); 3,8-4,1(4H, m, N⁺CH$_2$; OCH$_2$); 3,3(9H, s, N⁺(CH$_3$)$_3$); 2,8(2H, m, CH$_2$COO); 2,3(2H, m, COCH$_2$); 2,1(1H, m, CH(CH$_3$)$_2$); 1,6(2H, m, CH$_2$); 1,3(10H, m, broad); |

| Ex code | R | n | X⁻ | $[\alpha]_D^{25}$ | E.A. found | | | | | m.p. °C. | HPLC Rt min | NMR δ |
|---|---|---|---|---|---|---|---|---|---|---|---|---|
| | | | | | C | H | N | Cl | H₂O | | | |
| | | | | | | | | | | | | 1,0–0,9(9H, d+t, CH₃CH(CH₃)₂.D₂O |

```
ªColumn:       Nucleosil-SA (5μ) 1,2 mm, i.d. 4,0 mm
T:             40° C.
mobile phase:  (NH₄)₂HPO₄ 50 mM/CH₃CN 1:1 pH4 con H₃PO₄
flow:          0,75 ml/min
ᵇColumn:       Spherisorb-Cl (5μ) 1,2 mm i.d. 4,6 mm
T:             50° C.
mobile phase:  CH₃OH/KH₂PO₄ 50 mM 60:40
flow:          0,5 ml/min
ᶜColumn:       Spherisorb-Cl (5μ) 1,2 mm i.d. 4,6 mm
T:             50° C.
mobile phase:  CH₃OH/KH₂PO₄ 50 mM 70:30 pH 3,9 con H₃PO₄
flow:          0,5 ml/min
ᵈColumn:       Spherisorb-Cl (5μ) 1,2 mm i.d. 4,6 mm
T:             40° C.
mobile phase:  CH₃OH/KH₂PO₄ 50 mM 65:35 pH 4,5 con H₃PO₄
flow:          0,5 ml/min
ᵉColumn:       Nucleosil-SA (5μ) 1,2 mm, i.d. 4,0 mm
T:             30° C.
mobile phase:  (NH₄)₂HPO₄ 50 mM/CH₃CN 65:35 pH 3,5 con H₃PO₄
flow:          0,75 ml/min
ᶠColumn:       Spherisorb-Cl (5μ) 1,2 mm i.d. 4,6 mm
T:             40° C.
mobile phase:  CH₃OH/KH₂PO₄ 50 mM 65:35 pH 4,5 con H₃PO₄
flow:          1 ml/min
```

ASSESSMENT OF BEHAVIOUR AND MORTALITY IN MICE

The assessment of normal behaviour in mice was carried out following S. Irwin's method (Psychopharmacologia, 13, 222 [1968]). This method allows alterations in some behavioural, neurophysiologic and neurovegetative parameters to be detected, which are directly observable by the researcher. The study was conducted using male Crl:(CD-1)(ICR)BR mice (Charles River-Italy) weighing 22–25 g. following oral administration of the compounds suspended in carboxymethylcellulose (0.5% by weight in H₂O) to groups of 4 animals/dose.

The animals were continously kept under observation for five hours following treatment and twice a day in the subsequent five days. Mortality was also observed during the overall test period.

Assessment of behaviour and mortality in mice.

| Compound | dose | Symptoms | Mortality |
|---|---|---|---|
| ST 712 | 1000 | NONE | 0/4 |
| ST 722 | 1000 | salivation, diarrhoea | 0/4 |

IMMUNOTOXICOLOGICAL STUDIES

Some immunotoxicological results after oral ST 722 administration in mice are described hereinafter:

Test 1: Evaluation of the "in vitro-ex vivo" effect of repeated oral administrations of ST 722 on the primary antibody production (Jerne test) in the spleen of SRBC (Sheep Red Blood Cells) immunized mice.

Experimental procedure

Male B₆D2F₁ mice (C. River) aged 8 weeks (6 animals each group) were utilized.

The substance (ST 722) was administered per os at the dose of 100 mg/kg/day from day −2 through day +2 (immunization at day 0). The animals were immunized by intraperitoneal route with a concentration of 1.0×10⁸ cells/mouse in 0.2 ml of sterile saline.

Five days later, spleens to be submitted to teasing process were removed from the animals sacrificed by cervical dislocation. After standardization at 1.0×10⁷ cells/ml. the splenocytes (0.1 ml) were mixed with warm agar-Hank's (2 ml) and 10% SRBC in PBS (0.2 ml) and seeded in Petri dishes (samples tested in triplicates) and incubated at 37° C. for 60 min.

After addition of complement (2 ml of guinea pig serum diluted 1:10 in Tris buffer), samples were further incubated at 37° C. for 30 min. To block the haemolysis reaction, the Petri dishes were cooled at 4° C. and the haemolysis plaques were counted.

The antibody response to SRBC is expressed as number of plaque forming cells (PFC) per 1.0×10⁶ splenocytes as well as per spleen.

Results

The results indicated that the repeated (5 consecutive days) oral administrations of ST 722 did not cause a statistically significant modification in PFC number after the antigenic challenge (Table 1). These data exclude the existence of an immunotoxic effect on the antibody-producer B lymphocytes.

The weight of the lymphold organs (spleen and thymus) did not show values relating to a toxic effect as well (Tab. 1).

TABLE 1

Primary antibody production (Jerne test).
Evaluation of the number of PFC (x ± S.E.) in the spleen
of mice immunized with SRBC and treated per os with ST 722
at the dose of 100 mg/kg/day from day -2 through day +2
(immunization at day 0).

| Treatment | Body weight (g) | Spleen weight (mg) | Thymus weight (mg) | PFC/$10^6$ cells | PFC/ spleen |
|---|---|---|---|---|---|
| Control | 25.33 ± 0.38 | 95.50 ± 3.19 | 64.00 ± 1.51 | 202 ± 32 | 34228 ± 5064 |
| ST 722 | 25.12 ± 0.77 | 94.33 ± 4.12 | 59.50 ± 3.62 | 261 ± 34 | 44440 ± 6087 |

Test 2: Evaluation of the effect of repeated oral administrations of ST 722 on the weight of murine lymphoid organs (spleen and thymus).

Experimental procedure

Male $B_6D_2F_1$ mice (C. River) aged 7 weeks (7-8 animals each group) were orally treated with the substance ST 722 at the dose of 100 mg/kg/day for 7 consecutive days. Twenty-four hours after the last administration, the animals were sacrificed, the organs removed and weighed.

Results

The performed treatment did not provoke any immunotoxic effect on the parameters examined (Table 2).

TABLE 2

Weight (x ± S.E.) of murine lymphoid organs
after repeated treatment oral of the animals with the
substance ST 722 (100 mg/kg/day for 7 consecutive days).

| Treatment | Body weight[a] (g) | Spleen weight[a] (mg) | Thymus weight[a] (mg) |
|---|---|---|---|
| Control | 24.00 ± 0.68 | 79.63 ± 3.31 | 51.88 ± 2.72 |
| ST 722 | 22.74 ± 0.37 | 77.88 ± 2.38 | 52.88 ± 3.20 |

[a] = mean value (x ± E.S.) of 7-8 samples.

Test 3: Evaluation of the effect of repeated oral administrations of ST 722 on the body, spleen and thymus weight, and on the splenocyte concentration in mice.

Experimental procedure

Male $B_6D_2F_1$ mice (C. River) aged 10 weeks (5 animals each group) were orally treated with the substance ST 722 at the dose of 100 mg/kg/day for 5 consecutive days. Twenty-four hours after the last administration, the animals were sacrificed, the organs removed and weighed, and the splenocyte number determined.

Results

The results, reported in Table 3, showed a lack of specific immunotoxic effects on the considered parameters following the scheduled ST 722 treatment.

TABLE 3

Weight of lymphoid organs and spleen concentration after
repeated oral treatments of mice with the substance ST 722
(100 mg/kg/day for 5 consecutive days).

| Treatment | Body weight[a] (g) | Spleen weight[a] (mg) | Thymus weight[a] (mg) | Splenoc. number[b] (× $10^{-7}$) |
|---|---|---|---|---|
| Control | 27.70 ± 0.48 | 75.75 ± 2.36 | 41.75 ± 3.59 | 7.90 |
| ST 722 | 26.50 ± 0.53 | 73.25 ± 3.84 | 38.80 ± 3.01 | 7.85 |

[a] = mean value (x ± S.E.) of 5 samples.
[b] = value from 5 pooled samples.

Test 4: Evaluation of the effect of repeated oral administrations of ST 722 on the peritoneal macrophage number in mice.

Experimental procedure

Male $B_6D_2F_1$ mice (C. River) aged 10 weeks (6 animals each group) were orally treated with the substance ST 722 at the dose of 100 mg/kg/day for 5 consecutive days. Twenty-four hours after the last administration, the animals were sacrificed, the peritoneal exudate cells (PEC) collected and the macrophage number determined.

Results

No toxic effect has been observed in PEC macrophage population; on the contrary, we measured an increase of about 60% in the peritoneal macrophages number of mice treated with the substance ST 722 (Table 4).

TABLE 4

Peritoneal macrophage (Mφ) number in mice treated with ST 722
(100 mg/kg/day for 5 consecutive days).

| Treatment | Body weight (g)[a] | PEC/ mouse[b] (× $10^6$) | PEC Mφ[b] (%) | PEC Mφ/ mouse[b] (× $10^6$) |
|---|---|---|---|---|
| Control | 28.07 ± 0.63 | 2.14 | 53 | 1.13 |
| ST 722 | 28.13 ± 1.30 | 2.86 | 63 | 1.80 |

TABLE 4-continued

Peritoneal macrophage (Mø) number in mice treated with ST 722 (100 mg/kg/day for 5 consecutive days).

| Treatment | Body weight (g)[a] | PEC/ mouse[b] (× 10⁻⁶) | PEC Mø[b] (%) | PEC Mø/ mouse[b] (× 10⁻⁶) |
|---|---|---|---|---|

[a] = mean value (± S.E.) of 6 animals.
[b] = Value from 6 pooled samples.

Evaluation of the Minimal Inhibitory Concentration (MIC) of 16 new substances for yeast and yeast-like strains.

Experimental procedure

The following strains were used (the number of strains is in brackets): Candida (13); Criptococcus (2); Saccharormyces (1); Torulopsis (1).

The tested substances were: ST 712, ST 722, ST 982, ST 983, ST 1000, ST 1001, ST. 1032, ST 1033, ST 1034, ST 1036, ST 1037, ST 1038, ST 1050, ST 1051, ST 1052, ST 1053.

Yeast Nitrogen Base supplemented with 0.15% asparagine and 1.0% glucose (as carbon source) was the medium utilized in the assays.

This medium was buffered with 0.165 M 2-(N-morpholino) propane sulfonic acid (MOPS), a non-chelating buffer.

The test was performed following the standard microdilution procedure and the inoculum suggestions of Pfaller (PFALLER M., RINALDI M. G., GALGIANI J. N., BARTLETT M. S., BODY B. A., ESPINELINGROFF A., FROMTLING R. A., HALL G. S., HUGHES G. E., ODDS F. C. and SUGAR A. M., 1990. *Collaborative investigation of variables in susceptibility testing of yeasts.* Antimicrob, Agents Chemother, Sep. 34, 9: 1648–1654) with COOK's modifications (COOK R., Mc INTYRE K. A. and GALGIANI J. M.,1990. *Effect of incubation temperature, inoculum size, and medium on agreement of macro-and microdilution broth susceptibility test, results for yeasts.* Antimicrob. Agents Cheroother. Aug. 34.8:1542–1545).

The inoculum was prepared from an overnight broth culture (a 48-hour culture only for Cryptococcus) in Sabouraud broth and appropriately diluted to yield a final suspension containing approximately $5.0 \times 10^6$ Colony Forming Units per ml (CFU/ml), when compared to the Mc Farland's standard control (BRAY W. E., *Clinical Laboratory Methods*, 5th Ed. C. V. MOSBY, St. Louis, Mo, 1957).

After further diluting (1:50), a 0.150-µl volume of such fungal suspensions and an equal volume of the substance solutions were distributed into each well of a microtiter plate (96 wells, round bottom). Such a procedure eventually allowed for an "in vitro" antimycotic activity assay utilizing final fungal inocula of approximately $5.0 \times 10^4$ CFU/ml.

MIC evaluation

After incubating the microtiter plates for 48 hours at 35° C., the MIC for each strain was determined, which is defined as the lowest concentration of the test substance where no visible fungal growth occurs.

MFC evaluation

The minimal fungicidal concentration was evaluated by spot-transferring onto Petri dishes, containing Sabouraud agar, 0.01-ml volumes of all the samples showing no visible fungal growth.

After incubation for 48 hours at 35° C., the MFC was determined, which is defined as the lowest concentration of the test substance that does not allow growth of agar subcultures.

Results

The MIC values, determined after incubating samples for 48 hours at 35° C., and illustrated in Table 1–6, are exactely equal to MFC values (data not shown), proving that these substances possess a lytic and not a simple antiproliferative activity against the tested strains.

TABLE 1

Minimal Inhibitory Concentration (mcg/ml) of 5 Isovaleryl L-Carnitine esters for yeast-like fungi.

| Strains | ST 1032 | ST 722 | ST 1037 | ST 1033 | ST 1001 |
|---|---|---|---|---|---|
| Candida albicans (562) | n.d. | 3.12 | 1.56 | 1.56 | 3.12 |
| Candida albicans (A 54) | n.d. | 3.12 | 1.56 | 1.56 | 3.12 |
| Candida albicans (ATCC 2091) | n.d. | 3.12 | 1.56 | 3.12 | 6.25 |
| Candida albicans (Ca 2) | n.d. | 1.56 | 1.56 | n.d. | 3.12 |
| Candida albicans (PG) | 25 | 3.12 | 3.12 | 3.12 | 6.25 |
| Candida albicans (ISS 1) | 25 | 1.56 | 3.12 | 1.56 | 12.5 |
| Candida glabrata (ISS 1) | n.d. | 6.25 | 3.12 | 3.12 | 6.25 |
| Candida guilliermondii (ISS 1) | n.d. | 6.25 | 6.25 | 6.25 | 6.25 |
| Candida krusei (ISS 1) | n.d. | 3.12 | 1.56 | 3.12 | 6.25 |
| Candida parapsilosis (ISS 1) | n.d. | 6.25 | 3.12 | 3.12 | 6.25 |
| Candida pseudotropicalis (EC 1) | n.d. | 6.25 | 6.25 | 3.12 | 12.5 |
| Candida tropicalis (5705) | n.d. | 3.12 | 3.12 | 3.12 | 6.25 |
| Candida tropicalis (ISS 1) | 12.5 | 3.12 | 3.12 | 3.12 | 12.5 |
| Cryptococcus neoformans (4711) | n.d. | 1.56 | 0.78 | 0.78 | 1.56 |
| Cryptococcus neoformans (ISS 1) | 50 | 3.12 | 1.56 | 1.56 | 3.12 |
| Saccharomyces cerevisiae (ATCC 7752) | 100 | 3.12 | 3.12 | 3.12 | 6.25 |
| Torulopsis candida (D.S.) | n.d. | 6.25 | 3.12 | 3.12 | 6.25 | n.d. = not determined.

TABLE 2

Mean MIC values (mcg/ml) of
5 Isovaleryl L-Carnitine esters for yeast-like fungi.

| Compound | Mean MIC values* | Tested strains | Resistant strains (MIC > 100) |
|---|---|---|---|
| ST 1032 | 42.50 | 5 | 0 |
| ST 722 | 3.76 | 17 | 0 |
| ST 1037 | 2.80 | 17 | 0 |
| ST 1033 | 2.70 | 17 | 0 |
| ST 1001 | 6.24 | 17 | 0 |

\* = Mean MIC values versus susceptible strains.

TABLE 3

Minimal Inhibitory Concentration (mcg/ml) of
6 Undecyl L-Carnitine esters for yeast-like fungi.

| Strains | ST 712 | ST 1034 | ST 1036 | ST 1000 | ST 982 | ST 983 |
|---|---|---|---|---|---|---|
| Candida albicans (562) | 12.5 | 1.56 | 1.56 | n.d. | n.d. | n.d. |
| Candida albicans (A 54) | 12.5 | 1.56 | 1.56 | 6.25 | >100 | >100 |
| Candida albicans (ATCC 2091) | 12.5 | 1.56 | 1.56 | n.d. | n.d. | n.d. |
| Candida albicans (Ca 2) | 6.25 | 1.56 | 1.56 | 1.56 | >100 | >100 |
| Candida albicans (PG) | 12.5 | 3.12 | 3.12 | n.d. | n.d. | n.d. |
| Candida albicans (ISS 1) | n.d. | 1.56 | 1.56 | 3.12 | n.d. | n.d. |
| Candida glabrata (ISS 1) | n.d. | 3.12 | 3.12 | 6.25 | n.d. | n.d. |
| Candida guilliermondii (ISS 1) | n.d. | 6.25 | 6.25 | 6.25 | n.d. | n.d. |
| Candida krusei (ISS 1) | n.d. | 1.56 | 1.56 | 1.56 | n.d. | n.d. |
| Candida parapsilosis (ISS 1) | n.d. | 6.25 | 6.25 | 6.25 | n.d. | n.d. |
| Candida pseudotropicalis (EC 1) | 12.5 | 6.25 | 6.25 | n.d. | n.d. | n.d. |
| Candida tropicalis (5705) | 3.12 | 3.12 | 3.12 | n.d. | >100 | >100 |
| Candida tropicalis (ISS 1) | n.d. | 3.12 | 3.12 | 3.12 | n.d. | n.d. |
| Cryptococcus neoformans (4711) | 3.12 | 1.56 | 1.56 | 1.56 | >100 | >100 |
| Cryptococcus neoformans (ISS 1) | n.d. | 3.12 | 3.12 | n.d. | n.d. | n.d. |
| Saccharomyces cerevisiae (ATCC 7752) | 6.25 | 3.12 | 3.12 | n.d. | n.d. | n.d. |
| Torulopsis candida (D.S.) | 12.5 | 3.12 | 3.12 | 6.25 | >100 | >100 | n.d. = not determined.

TABLE 4

Mean MIC values (mcg/ml) of
6 Undecyl L-Carnitine esters for yeast-like fungi.

| Compound | Mean MIC values* | Tested strains | Resistant strains (MIC > 100) |
|---|---|---|---|
| ST 712 | 9.37 | 10 | 0 |
| ST 1034 | 3.03 | 17 | 0 |
| ST 1036 | 2.84 | 17 | 0 |
| ST 1000 | 4.21 | 10 | 0 |
| ST 982 | >100 | 5 | 5 |
| ST 983 | >100 | 5 | 5 |

\* = Mean MIC values versus susceptible strains.

TABLE 5

Minimal Inhibitory Concentration (mcg/ml) of
5 L-Carnitine esters for yeast-like fungi.

| Strains | ST 1038 | ST 1052 | ST 1051 | ST 1050 | ST 1053 |
|---|---|---|---|---|---|
| Candida albicans (562) | 3.12 | 3.12 | 3.12 | 6.25 | 12.5 |
| Candida albicans (A 54) | 3.12 | n.d. | n.d. | n.d. | n.d. |
| Candida albicans (ATCC 2091) | 3.12 | n.d. | n.d. | n.d. | n.d. |
| Candida albicans (Ca 2) | 1.56 | 1.56 | 1.56 | 3.12 | 3.12 |
| Candida albicans (PG) | 6.25 | n.d. | n.d. | n.d. | n.d. |
| Candida albicans (ISS 1) | 6.25 | n.d. | n.d. | n.d. | n.d. |
| Candida glabrata (ISS 1) | 6.25 | n.d. | n.d. | n.d. | n.d. |
| Candida guilliermondii (ISS 1) | 6.25 | n.d. | n.d. | n.d. | n.d. |
| Candida krusei (ISS 1) | 3.12 | 3.12 | 3.12 | 3.12 | 3.12 |
| Candida parapsilosis (ISS 1) | 6.25 | n.d. | n.d. | n.d. | n.d. |
| Candida pseudotropicalis (EC 1) | 6.25 | n.d. | n.d. | n.d. | n.d. |
| Candida tropicalis (5705) | 3.12 | 3.12 | 3.12 | 6.25 | 6.25 |
| Candida tropicalis (ISS 1) | 3.12 | n.d. | n.d. | n.d. | n.d. |
| Cryptococcus neoformans (4711) | 1.56 | n.d. | n.d. | n.d. | n.d. |
| Cryptococcus neoformans (ISS 1) | 3.12 | n.d. | n.d. | n.d. | n.d. |
| Saccharomyces cerevisiae (ATCC 7752) | 6.25 | 3.12 | 3.12 | 3.12 | 3.12 |
| Torulopsis candida (D.S.) | 6.25 | n.d. | n.d. | n.d. | n.d. | n.d. = not determined.

TABLE 6

Mean MIC values (mcg/ml) of
5 L-Carnitine esters for yeast-like fungi.

| Compound | Mean MIC values* | Tested strains | Resistant strains (MIC > 100) |
|---|---|---|---|
| ST 1038 | 4.40 | 17 | 0 |
| ST 1052 | 2.80 | 5 | 0 |
| ST 1051 | 2.80 | 5 | 0 |
| ST 1050 | 4.37 | 5 | 0 |
| ST 1053 | 5.62 | 5 | 0 |

\* = Mean MIC values versus susceptible strains.

Evaluation of Minimal Inhibitory Concentration (MIC) of 16 new substances for filamentous fungi.

Experimental procedure

The following strains were used (the number of strains is in brackets): Aspergillus (5); Fusarium (1); Mucor (1); Penicillium (1).

The tested substances were: ST 712, ST 722, ST 982, ST 983, ST 1000, ST 1001, ST 1032, ST 1033, ST 1034, ST 1036, ST 1037, ST 1038, ST 1050, ST 1051, ST 1052, ST 1053. The assay medium was the same as the one used in the previous study. The conidia from 72-hour cultures in Sabouraud agar, collected by washing with Sabouraud medium and Tween 80 (one drop of Tween per 10 ml of medium), were utilized as inoculum ($5.0 \times 10^4$ CFU/ml).

The assay was performed using the same procedure as described for yeast-like fungi.

Also the evaluation of MIC and MFC was as reported previously.

Results

The MIC values, reported in Tables 7–12, were exactly the same as the MFC values (data not shown), determined by a subculture tecnique.

TABLE 7

Minimal Inhibitory Concentration (mcg/ml) of 5 Isovaleryl L-Carnitine esters for filamentous fungi.

| Strains | ST 1032 | ST 722 | ST 1037 | ST 1033 | ST 1001 |
|---|---|---|---|---|---|
| Aspergillus fumigatus (ATCC 28212) | >100 | 12.5 | 6.25 | 3.12 | 6.25 |
| Aspergillus fumigatus (1/A) | n.d. | 12.5 | 6.25 | 3.12 | 6.25 |
| Aspergillus fumigatus (2/A) | n.d. | 12.5 | 6.25 | 3.12 | 6.25 |
| Aspergillus fumigatus (C/1) | n.d. | 12.5 | 6.25 | 3.12 | 6.25 |
| Aspergillus niger (ATCC 16404) | >100 | 12.5 | 6.25 | 6.25 | 12.5 |
| Mucor mucedo (ATCC 7941) | >100 | 50 | 12.5 | 6.25 | >100 |
| Fusarium sp. (ISS 1) | 100 | 6.25 | 3.12 | 3.12 | 12.5 |
| Penicillium sp. (1302) | 100 | 12.5 | 6.25 | 3.12 | 6.25 | n.d. = not determined.

TABLE 8

Mean MIC values (mcg/ml) of 5 Isovaleryl L-Carnitine esters for filamentous fungi.

| Compound | Mean MIC values* | Tested strains | Resistant strains (MIC > 100) |
|---|---|---|---|
| ST 1032 | 100 | 5 | 3 |
| ST 722 | 16.40 | 8 | 0 |
| ST 1037 | 6.64 | 8 | 0 |
| ST 1033 | 3.90 | 8 | 0 |
| ST 1001 | 7.03 | 8 | 1 |

* = Mean MIC values versus susceptible strains.

TABLE 9

Mean MIC values (mcg/ml) of 6 Undecyl L-Carnitine esters for filamentous fungi.

| Strains | ST 712 | ST 1034 | ST 1036 | ST 1000 | ST 982 | ST 983 |
|---|---|---|---|---|---|---|
| Aspergillus fumigatus (ATCC 28212) | 25 | 6.25 | 3.12 | 3.12 | >100 | >100 |
| Aspergillus fumigatus (1/A) | 25 | 6.25 | 6.25 | n.d. | n.d. | n.d. |
| Aspergillus fumigatus (2/A) | 25 | 3.12 | 6.25 | n.d. | n.d. | n.d. |
| Aspergillus fumigatus (C/1) | 25 | 6.25 | 3.12 | n.d. | n.d. | n.d. |
| Aspergillus niger (ATCC 16404) | 50 | 6.25 | 3.12 | 3.12 | >100 | >100 |
| Mucor mucedo (ATCC 7941) | 50 | 12.5 | 6.25 | 6.25 | >100 | >100 |
| Fusarium sp. (ISS 1) | n.d. | 3.12 | 3.12 | 3.12 | >100 | >100 |
| Penicillium sp. (1302) | n.d. | 3.12 | 3.12 | 3.12 | >100 | >100 | n.d. = not determined.

TABLE 10

Mean MIC values (mcg/ml) of 6 Undecyl L-Carnitine esters for filamentous fungi.

| Compound | Mean MIC values* | Tested strains | Resistant strains (MIC > 100) |
|---|---|---|---|
| ST 712 | 30.00 | 6 | 1 |
| ST 1034 | 5.85 | 8 | 0 |
| ST 1036 | 4.29 | 8 | 0 |
| ST 1000 | 3.76 | 5 | 0 |
| ST 982 | >100 | 5 | 5 |
| ST 983 | >100 | 5 | 5 |

* = Mean MIC values versus susceptible strains.

TABLE 11

Minimal Inhibitory Concentration (mcg/ml) of 5 L-Carnitine esters for filamentous fungi.

| Strains | ST 1038 | ST 1052 | ST 1050 | ST 1051 | ST 1053 |
|---|---|---|---|---|---|
| Aspergillus fumigatus (ATCC 28212) | 12.5 | 3.12 | 6.25 | 3.12 | 6.25 |
| Aspergillus fumigatus (1/A) | 12.5 | n.d. | n.d. | n.d. | n.d. |
| Aspergillus fumigatus (2/A) | 12.5 | n.d. | n.d. | n.d. | n.d. |
| Aspergillus fumigatus (C/1) | 6.25 | n.d. | n.d. | n.d. | n.d. |
| Aspergillus niger (ATCC 16404) | 12.5 | 3.12 | 6.25 | 6.25 | 3.12 |
| Mucor mucedo (ATCC 7941) | 25 | 6.25 | 12.5 | 6.25 | 12.5 |
| Fusarium sp. (ISS 1) | 6.25 | 6.25 | 6.25 | 6.25 | 6.25 |
| Penicillium sp. (1302) | 12.5 | 3.12 | 3.12 | 3.12 | 3.12 | n.d. = not determined.

TABLE 12

Mean MIC values (mcg/ml) of 5 L-Carnitine esters for filamentous fungi.

| Compound | Mean MIC values* | Tested strains | Resistant strains (MIC > 100) |
|---|---|---|---|
| ST 1038 | 12.50 | 8 | 0 |
| ST 1052 | 4.37 | 5 | 0 |
| ST 1050 | 6.85 | 5 | 0 |
| ST 1051 | 6.87 | 5 | 0 |
| ST 1053 | 6.24 | 5 | 0 |

* = Mean MIC values versus susceptible strains.

Evaluation of Minimal Inhibitory Concentration (MIC) of 7 new substances for dermatophytic fungi.

Experimental procedure

The following strains were used: *Trichophyton menthagrophytes* ATCC 9533, *Trichophyton rubrum* IHEM 4274, *Microsporum canis* IHEM 3522, *Epydermophyton floccosum* IHEM 3495. The tested substances were: ST 722, ST 1033, ST 1037, ST 1050, ST 1051, ST 1052,. ST 1053.

The assay was performed following the same procedure described for the yeasts, by using 7-day fungi cultures grown at 30° C. in Potato Dextrose agar, and harvested with Sabouraud broth and Tween 80 (0.5%).

After washing with Yeast Nitrogen Base, supplemented with asparagine and glucose ( as carbon source), the fungal suspension was fragmented using a tissue grinder until the largest clumps or aggregates were undetectable within the grinder. This fungal suspension was then appropriately diluted in YNB to yield a concentration of $2.0 \times 10^5$ infective particles/ml (small mycelium fragments, micro-and macroaleuriospores).

Volumes of 100 μl both of the fungal suspensions and substance solutions, two-fold serially diluted in assay medium, were distributed into each well of a microtiter plate (96 wells, round bottom), which was incubated at 35° C. for 96 hours.

The MIC values, substantially corresponding to the MFC values (data not shown), are reported in Table 13-14.

TABLE 13

Minimal Inhibitory Concentration (mcg/ml) of 7 new substances for dermatophytic fungi.

| Strains | ST 722 | ST 1037 | ST 1033 | ST 1052 | ST 1050 | ST 1051 | ST 1053 |
|---|---|---|---|---|---|---|---|
| Epidermophyton floccosum (IHEM 3495) | 50 | 25 | 25 | 25 | 50 | 25 | 50 |
| Microsporum canis (IHEM 3522) | 25 | 12.5 | 6.25 | 6.25 | 12.5 | 12.5 | 6.25 |
| Trichophyton rubrum (IHEM 4274) | 12.5 | 6.25 | 6.25 | 6.25 | 6.25 | 6.25 | 6.25 |
| Trichophyton menthagrophites (ATCC 9533) | 25 | 12.5 | 12.5 | 12.5 | 12.5 | 12.5 | 6.25 |

TABLE 14

Mean MIC values (mcg/ml) of 7 new substances for dermatophytic fungi.

| Compound | Mean MIC values* | Tested strains | Resistant strains (MIC > 100) |
|---|---|---|---|
| ST 722 | 28.12 | 4 | 0 |
| ST 1037 | 14.06 | 4 | 0 |
| ST 1033 | 12.50 | 4 | 0 |
| ST 1052 | 12.50 | 4 | 0 |
| ST 1050 | 20.31 | 4 | 0 |
| ST 1051 | 14.06 | 4 | 0 |
| ST 1053 | 14.06 | 4 | 0 |

\* = Mean MIC values versus susceptible strains.

Evaluation of the protective effects of ST 722 in an experimental subcutaneous infection with *Candida albicans* in mice.

Experimental procedure

Animals

Male $CD_1$ outbred mice (IFFA Credo) aged 8 weeks were used (4 animals per group).

Bacterial strain

A pathogenic strain of Candida was used, namely *C. albicans* ISS 1. The MIC of ST 722 against this strain was 1.56 mcg/ml, whereas the MIC of Miconazole, a reference compound, was not determined, although the data available from the literature indicate MIC values raging from 0.5 to 10 mcg/ml.

Compounds

The infected animals were treated with ST 722 dissolved in saline, and Miconazole diluted in saline from a stock solution containing 1% Dimethyl Formamide.

Infective model

From an overnight broth culture of *C. albicans* in Sabouraud broth, a fungal suspension was prepared in sterile saline containing $5.0 \times 10^5$ cells/ml. An inoculum of 0.5 ml of this suspension was injected subcutaneously into the abdominal wall of each animal.

The compounds were then administered by subcutaneous injection in the same area of the fungal challenge at the dose of 50 mcg (in 0.2 ml of saline) immediately after the inoculum and following 48 and 96 hours (150 total mcg per animal).

Then, 48 hours following the last treatment (6 days after the challenge with Candida), the animals were sacrificed, and the abdominal wall as well as the peritoneum were dissected out.

The excised tissues were then homogenized in 5 ml of sterile saline with a Potter-Elvehjem tissue grinder. The resulting suspensions, appropriately diluted, where plated onto Petri dishes containing a selective agar medium (BIGGY agar), which allows to easily detect the yeast Colony Forming Units (CFU/ml).

Evaluation of results

The number of colonies scored in a series of dilutions for each single sample consents to calculate the number of yeast cells present in the infected tissue sample as follows:

$$\text{Number of yeast cells} = \frac{\Sigma C_i}{\Sigma N_i Z_i}$$

Where $Z_i$ is the number of dilutions performed, $N_i$ is the number of plates prepared for each dilution, and $C_i$ is the total number of yeast cells scored in each dilution.

Results

The results reported in Table 1 show that ST 722, administered as described above, substantially inhibits the infection with Candida, inducing the disappearance of Candida cells from the abdomen of treated animals (3 sterile samples out of 4). Similar experimental results were attained with Miconazole.

TABLE 1

Effect of ST 722 and Miconazole (reference compound) in an experimental subcutaneous infection with *Candida albicans* in mice.

| Treatment | Sample | CFU/mouse |
|---|---|---|
| Control | 1-4 | $1.19 \times 10^4$(*) |
| ST 722 | 1 | sterile |
|  | 2 | sterile |
|  | 3 | sterile |
|  | 4 | $1.36 \times 10^2$ |
| Miconazole | 1 | sterile |
|  | 2 | sterile |
|  | 3 | $3.60 \times 10^1$ |
|  | 4 | $8.10 \times 10^1$ |

(*) = Mean CFU value of 4 control samples.

Evaluation of the protective effect of ST 722 in a systemic experimental infection with *Candida albicans* in mice.

Experimental procedure

Animal

Male CD1 mice (C. River) aged 6 or 13 weeks were used (12–15 animals per group).

Yeast strain

The pathogenic strain of Candida utilized, i.e. *C. albicans* PG, was able, when inoculated intravenously, to cause multiple renal lesions and systemic dissemination, provoking death of the animals within 40 days from the challenge. The compound ST 722 exibits against this Candida strain a value of MIC and MFC equal to 3.12 mcg/ml.

Inoculum preparation

A broth culture in Sabouraud broth is prepared from a 48-hour agar slant culture.

After incubation for 48 hours at 37° C., the broth culture is first washed 3 times with sterile saline, then adjusted to a concentration of $2.0 \times 10^6$ cells/ml. Volumes of 0.25 ml of this suspension are i.v. injected into the animals, with a resulting infective dose approximately corresponding to DL100.

Treatment

ST 722 was administered per os following two different protocols:

I) 100 mg/kg administered at +2, +12, +24, +36 and +48 hours (i.e. 5 administrations in two days) with respect to the challenge.

II) 100 mg/kg administered twice daily on 6 consecutive days (i.e. 12 adimistrations) starting from day −2 to day +3 with respect to the day of inoculation (day 0).

Evaluation criteria

After the challenge, the animals were followed up for 60 days, and the percent mortality as well as the mean survival time (MST) were evaluated. The statistical significance of the results was evaluated by means of Fisher "exact test" and Mann-Withney "U" test, respectively.

Results

The protective effect of ST 722. only in terms of MST prolongation, was confirmed in both protocol I and II. In fact, also in protocol II the percent mortality of mice was completely unaffected, although the number of administrations was raised and the ST 722 treatment was started two days prior to the challenge (Table 2 and 3 ).

TABLE 2

Protective effect of ST 722 in mice experimentally infected with a *C. albicans* pathogenic strain.

| Treatment | Dead /Total | % Mortality | MST (days)[a] |
|---|---|---|---|
| Control | 13/15 | 86.6 | 22 (15–30) |
| ST 722[b] | 10/14 | 71.4 | 37 (25–≧60)▲ |

[a] = Mean survival time (range of variation is in brackets). The animals were followed up for 60 consecutive days after challenge (day 0).

TABLE 2-continued

Protective effect of ST 722 in mice experimentally infected with a *C. albicans* pathogenic strain.

| Treatment | Dead /Total | % Mortality | MST (days)[a] |
|---|---|---|---|

[b] = The substance was administered according to protocol I.
▲ = $p \leq 0.05$ (Mann-Withney "U" test).

TABLE 3

Protective effect of ST 722 in mice experimentally infected with a *C. albicans* pathogenic strain.

| Treatment | Dead/Total | % Mortality | MST (days)[a] |
|---|---|---|---|
| Control | 10/12 | 83.3 | 26 (22–39) |
| ST 722[b] | 10/14 | 71.4 | 44 (32–≧60)▲ |

[a] = Mean survival time (range of variation is in brackets). The animals were followed up for 60 consecutive days after challenge (day 0).
[b] = The substance was administered according to protocol II.
▲ = $p \leq 0.05$ (Mann-Withney "U" test).

We claim:

1. The method for treating a mycosis in a human or animal which comprises administering to the human or animal an antimycotic effective amount of an ester of acyl L-carnitine of the general formula, $$\begin{array}{c} CH_3 \\ CH_3-N^+-CH_2-CH(O-CO-(CH_2)_n-CH_3)-CH_2-CO-O-R \\ CH_3 \quad X^- \end{array} \quad (I)$$

wherein:

R is an straight or branched saturated aliphatic hydrocarbon carboxylic acyl group having 2–16 carbon atoms, n is an integer from 7 to 15, and X is the anion of a pharmacologically acceptable acid.

2. The method of claim 1, wherein the mycosis is an infection by a yeast.

3. The method of claim 2, wherein the mycosis is an infection sustained by *Candida albicans, Candida tropicalis, Candida pseudotropicalis, Torulopsis candida, Saccharomices cerevisiae* or *Cryptococcus neoformans*.

4. The method of claim 1, wherein the mycosis is an infection by a filamentous fungus.

5. The method of claim 4, wherein the mycosis is an infection sustained by Aspergillus fumigatus, Aspergillus niger,or *Mucor mucedo*.

6. The method of claim 1 wherein R is isobutyryl or isovaleryl.

7. The method of claim 1 wherein n is 10.

8. The method of claim 1 wherein X is selected from: chloride; bromide; iodide; acid aspartate; acid citrate; tartrate; acid phosphate; acid fumarate; glycerophosphate; glucosephosphate; lactate; acid maleate; orotate; acid oxalate; acid sulphate; trichloroacetate, trifluoroacetate and methansulphonate.

9. The method of claim 1 wherein the ester is isovalery L-carnitine undecyl ester chloride.

10. The method of claim 1 wherein the ester is isobutyryl L-carnitine undecyl ester chloride.

* * * * *